United States Patent [19]

Janfaza

[11] Patent Number: 5,295,477
[45] Date of Patent: Mar. 22, 1994

[54] ENDOSCOPIC OPERATING MICROSCOPE

[76] Inventor: Parviz Janfaza, 3 Liberty St., Natick, Mass. 01760

[21] Appl. No.: 880,530

[22] Filed: May 8, 1992

[51] Int. Cl.$^5$ .............................................. A61B 1/06
[52] U.S. Cl. ...................................... 126/6; 359/368; 359/365; 348/45
[58] Field of Search .................. 128/6, 4; 358/98, 88; 359/368, 385

[56] References Cited

U.S. PATENT DOCUMENTS

| | | | |
|---|---|---|---|
| 4,395,731 | 7/1983 | Schoolman | 358/98 |
| 4,651,201 | 3/1987 | Schoolman | 128/6 X |
| 4,760,840 | 8/1988 | Fournier, Jr. et al. | 128/6 X |
| 4,805,027 | 2/1989 | Sluyter | 128/6 X |
| 4,836,188 | 6/1989 | Berry | 128/6 |
| 4,890,159 | 12/1989 | Ogiu | 128/6 X |
| 4,924,853 | 5/1990 | Jones, Jr. et al. | 358/98 X |
| 5,174,277 | 12/1992 | Matsumaru | 128/4 |

Primary Examiner—Richard J. Apley
Assistant Examiner—Beverly A. Meindl
Attorney, Agent, or Firm—Herbert L. Bello

[57] ABSTRACT

Disclosed is a surgical apparatus which provides multi-dimensional views of the internal area of a biological specimen. The apparatus includes an endoscope connected to an operating microscope. The endoscope can be a sleeve formed by a series of collar elements or a rigid rod. The endoscope contains a guide or lens means for transmitting an optical image and an illuminating means for the transmission of light. A moveable prism is positioned on the end of each of the guide or lens means and serves to enlarge the apparatuses field of view as well as enhance stereoscopic imaging.

20 Claims, 7 Drawing Sheets

ENDOSCOPIC OPERATING MICROSCOPE

BACKGROUND OF THE INVENTION

1. Field of the Invention

The present invention relates to an endoscopic system and, more particularly, is directed to an apparatus utilizing an endoscope in conjunction with an operating microscope to provide multidimensional views of the internal area of a biological specimen.

2. Description of the Prior Art

Endoscopes are widely used for observing the internal organs of humans and other large biological specimens. The use of this instrument permits investigation of organs without the need for invasive and traumatizing surgical procedures. Endoscopes are used for diagnostic, research, and surgical purposes.

In use, a doctor holds the endoscope while inserting one end into the specimen's body via an incision or opening in either the respiratory system or gastrointestinal tract. Once through the incision or opening, the end of the endoscope is maneuvered into a passageway leading to the specific area to be observed. Generally, the surgeon holds the endoscope in one hand while performing the desired surgical procedure with the other hand.

The area to be observed can be viewed by direct visual observation or magnification using, for example, television relay systems. Exemplary imaging systems are described in U.S. Pat. Nos. 4,615,332, 4,862,873 and 4,890,159. Although fiber optic systems are capable of providing images, such systems suffer from the limitation that they provide only a two-dimensional view of the object or surface being investigated. As a result, surface topography and spacial orientations are not clearly discernable. The inability of the image to provide depth perception limits the usefulness of endoscopes.

Accordingly, there exists a need for a stereoscopic endoscope which provides high resolution images with depth perception and permits a doctor to have substantially free movement of both hands during surgical procedures.

SUMMARY OF THE INVENTION

It is an object of the present invention to provide an endoscope which does not suffer from the foregoing disadvantages and limitations.

It is a another object of the invention to provide an endoscopic apparatus which permits multidimensional viewing of the internal areas of biological specimens.

It is a further object of the invention to provide an endoscopic examination apparatus which permits a surgeon to use both hands while performing medical procedures.

It is yet another object of the invention to provide an apparatus for high resolution imaging with depth perception of the internal areas of a biological specimen.

Other general and specific objects of the invention will in part be obvious and will in part appear hereinafter.

The present invention is characterized by an operating endoscopic microscope that is sized and shaped to be inserted into a cavity or incision in a biological specimen for high resolution, depth perception viewing of selected areas in the specimen.

The endoscope has an observation end and an insertion end. The insertion end preferably is a sleeve formed by a series of collar elements which are pivotally connected to each other and contain a guide or lens means through which an optical image can be transmitted. Typical guide means are fiber-optic bundles arranged either singularly or in pairs. The lens means can be composed of either a single, or paired, series of optically aligned lenses. A moveable prism is positioned on the end of each of the guide or lens means. Preferably, when pairs of fiber-optic bundles, or optically aligned lens, are utilized the prisms are oriented so as to provide convergent fields of view which enhance stereoscopic imaging. The sleeve typically also contains an illuminating means for transmitting light into the biological specimen. A light source means supplies the requisite light to the illuminating means. Elements for locking the sleeve in selected positions, or rotating it about its longitudinal axis, can also be provided.

The operating microscope is operatively connected to the observation end of the endoscope and, preferably, is configured to be free-standing. An optical connecting means connects the ocular openings of the microscope to the guide or lens means of the endoscope. A pair of viewing ports are provided for binocular viewing of the transmitted image. When only a single guide or lens means is utilized, a prism means can be included in the microscope. This prism means splits the image transmitted by the endoscope and transmits it to each of the ocular openings. Thus, the prism means permits a single guide or lens means to provide binocular viewing of the transmitted image. In order to present the user with an upright image, the microscope also includes a lens system which inverts the optical image transmitted by the guide or lens means. The inversion system is operatively connected to the observation end of the endoscope and may be a component of the optical connecting means.

The invention accordingly comprises the steps and apparatus embodying features of construction, combinations of elements and arrangements of parts adapted to effect such steps, as exemplified in the following detailed disclosure. The scope of the invention is indicated in the claims.

BRIEF DESCRIPTION OF THE DRAWINGS

A fuller understanding of the nature and objects of the present invention will become apparent upon consideration of the following detailed description taken in connection with the accompanying drawings, wherein.

DETAILED DESCRIPTION OF THE PREFERRED EMBODIMENTS

Figure 1:
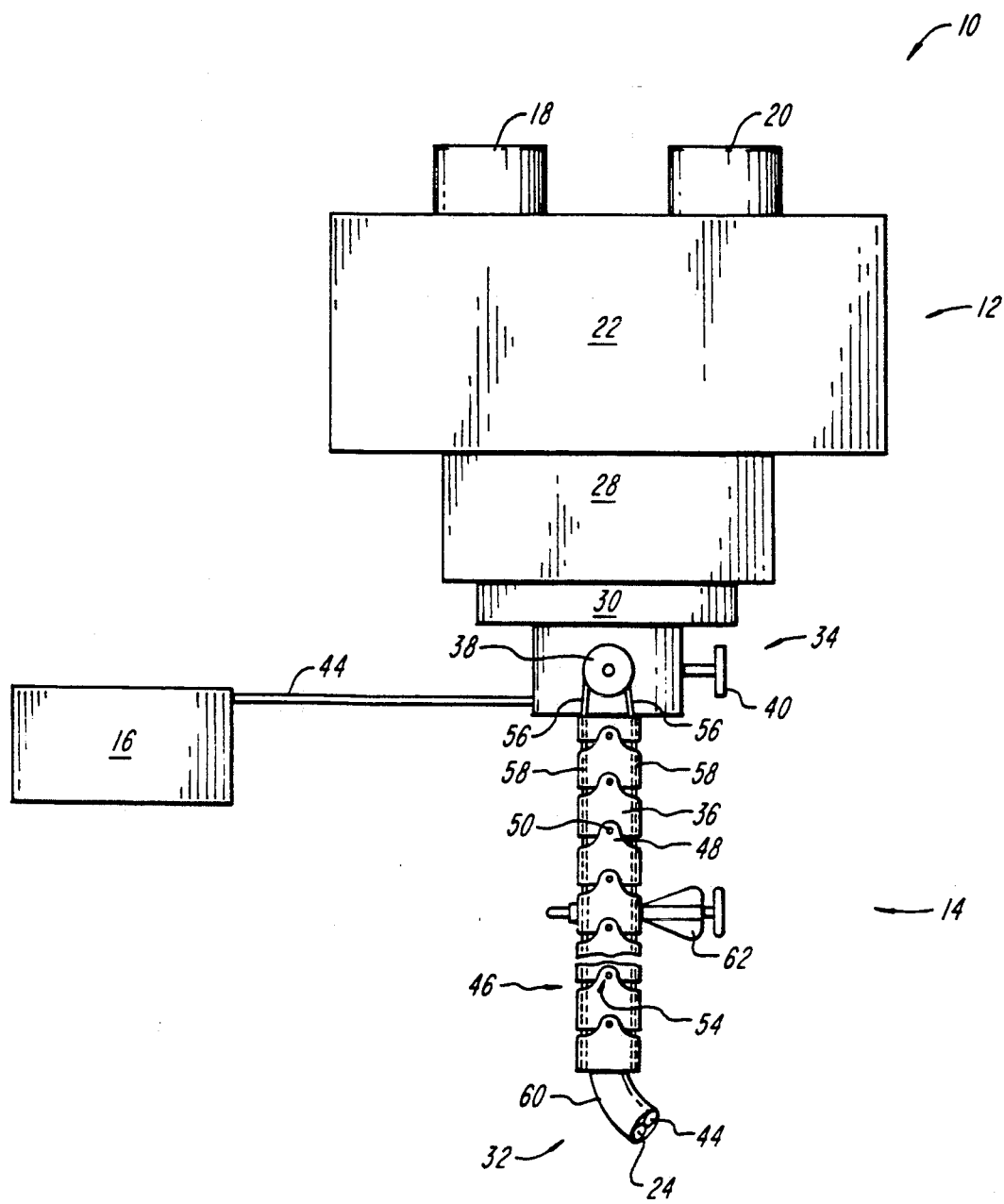
FIG. 1 is a front view of a first embodiment of the invention having a flexible sleeve containing a single guide means for transmitting an image.
Figure 2:
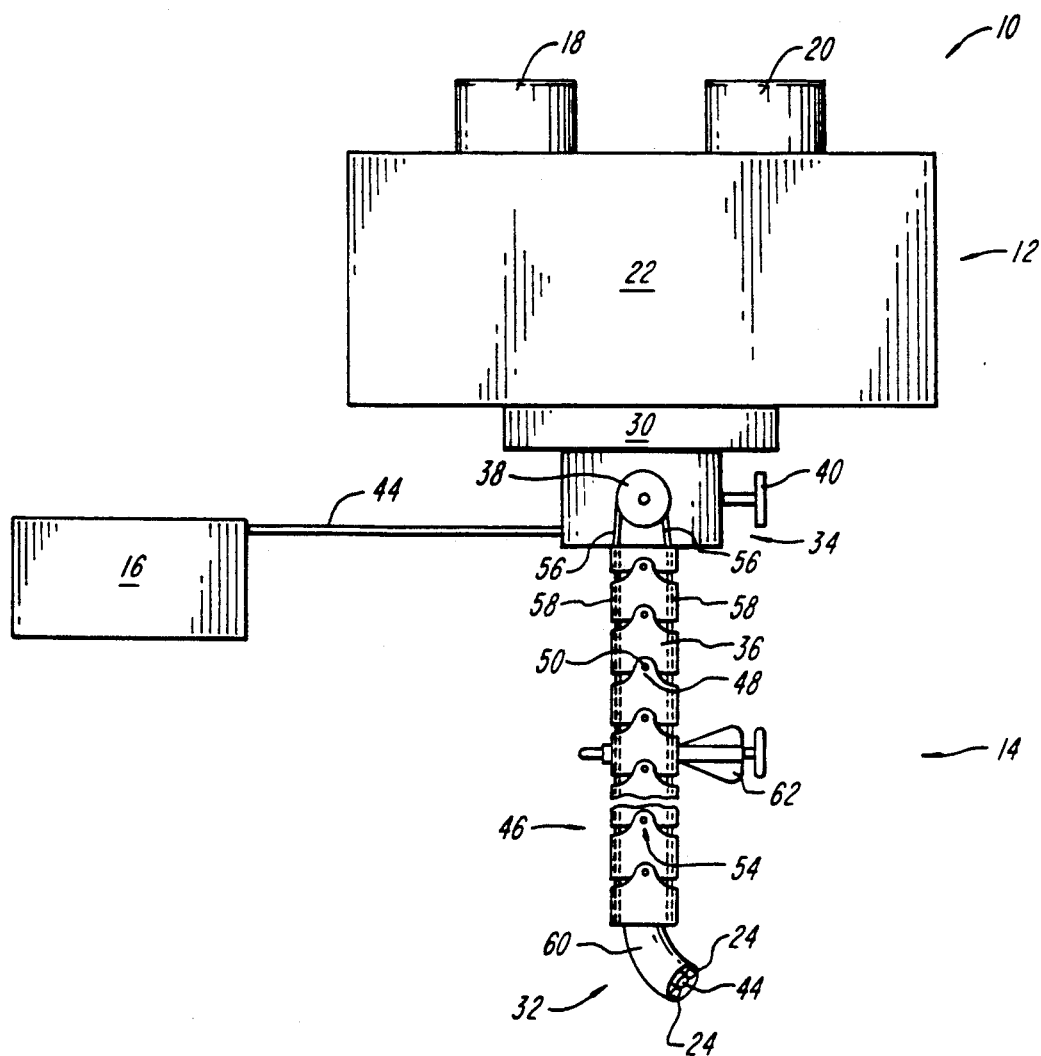
FIG. 2 is a front view of the first embodiment of the invention depicted in FIG. 1 having a flexible sleeve containing a pair guide means.
Figure 3:
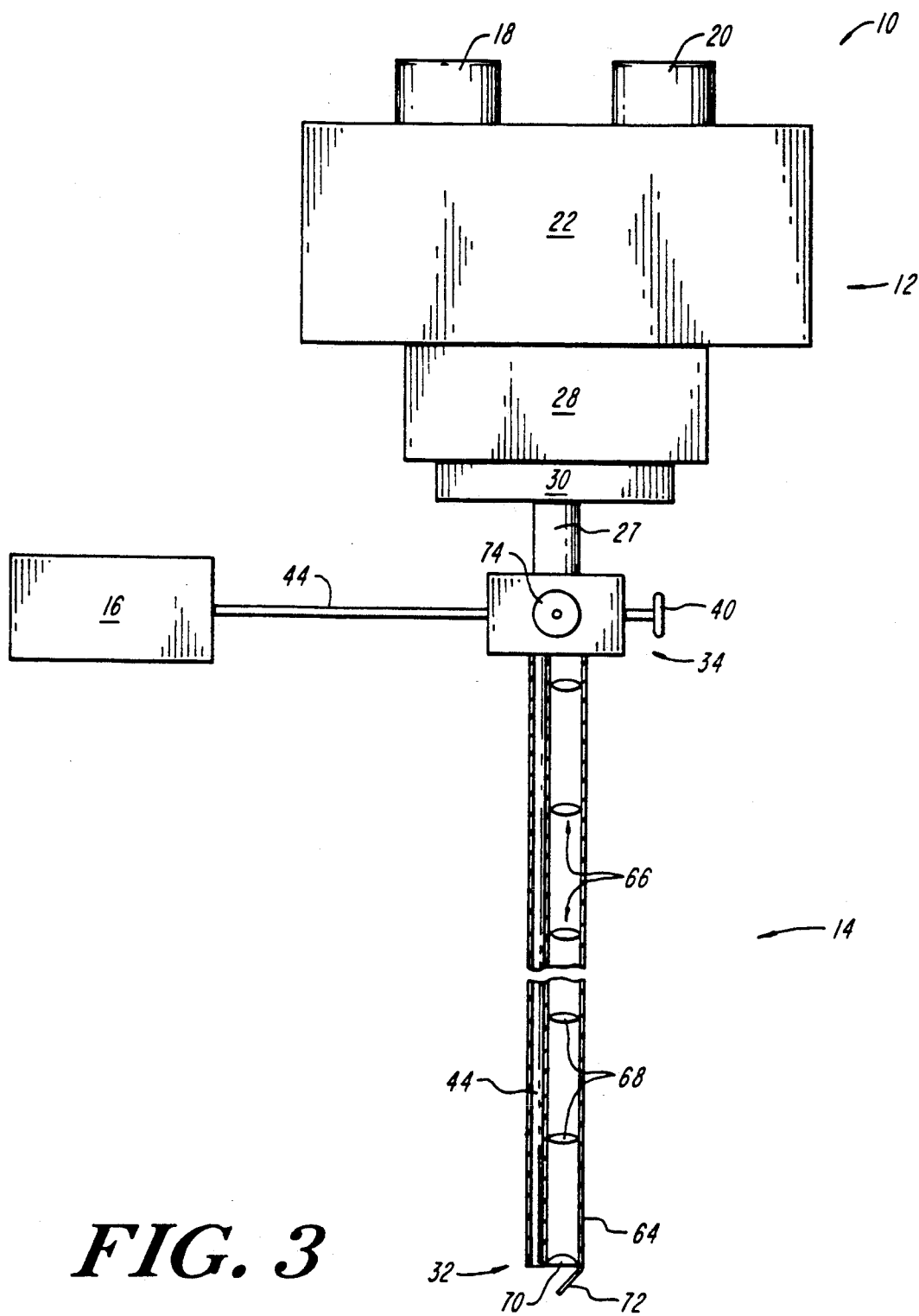
FIG. 3 is a front view of a second embodiment of the invention having a rigid sleeve containing a single lens system for transmitting an image.
Figure 4:
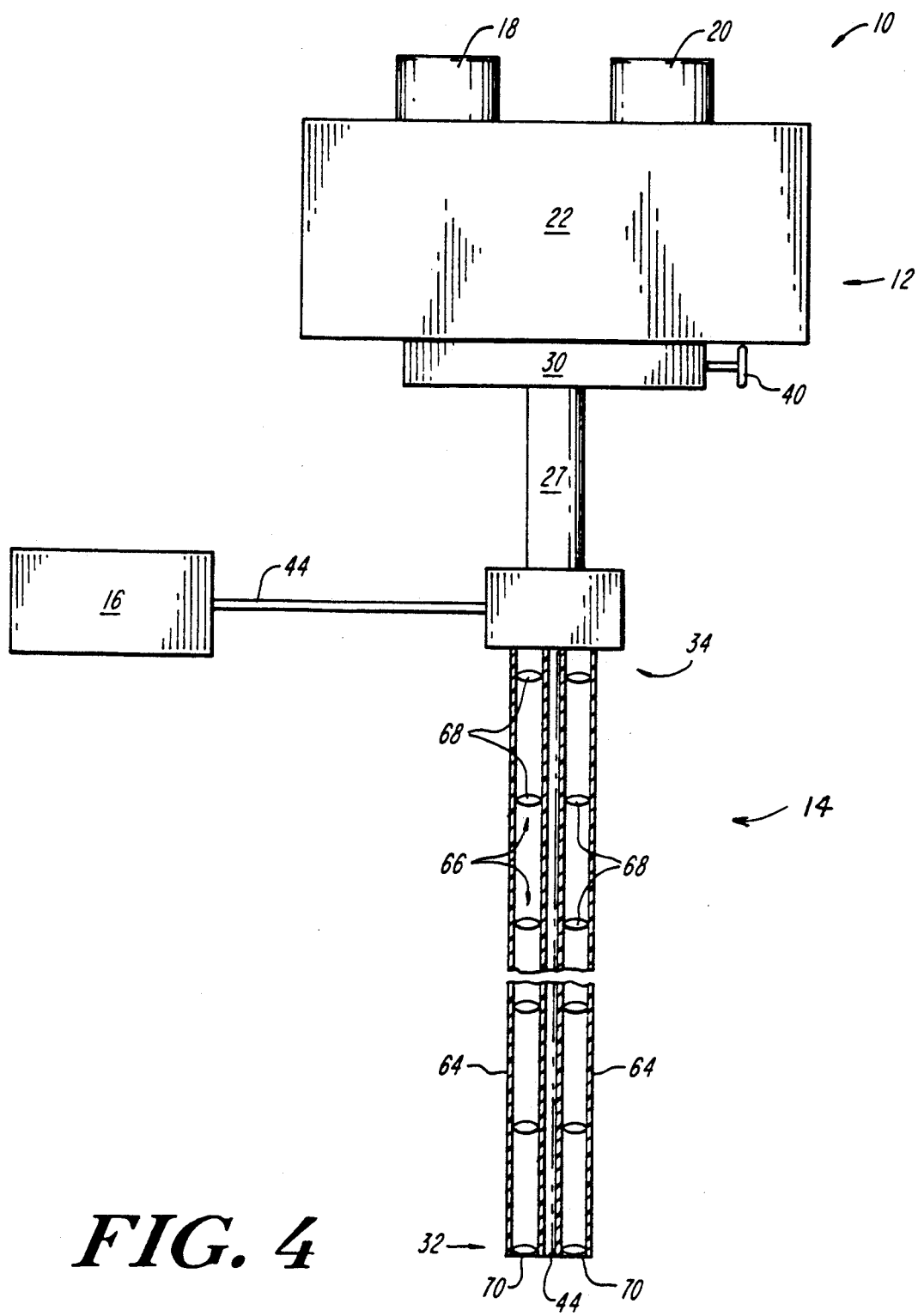
FIG. 4 is a front view of the second embodiment of the invention depicted in FIG. 3 having a rigid sleeve containing a pair lens systems.
Figure 5:
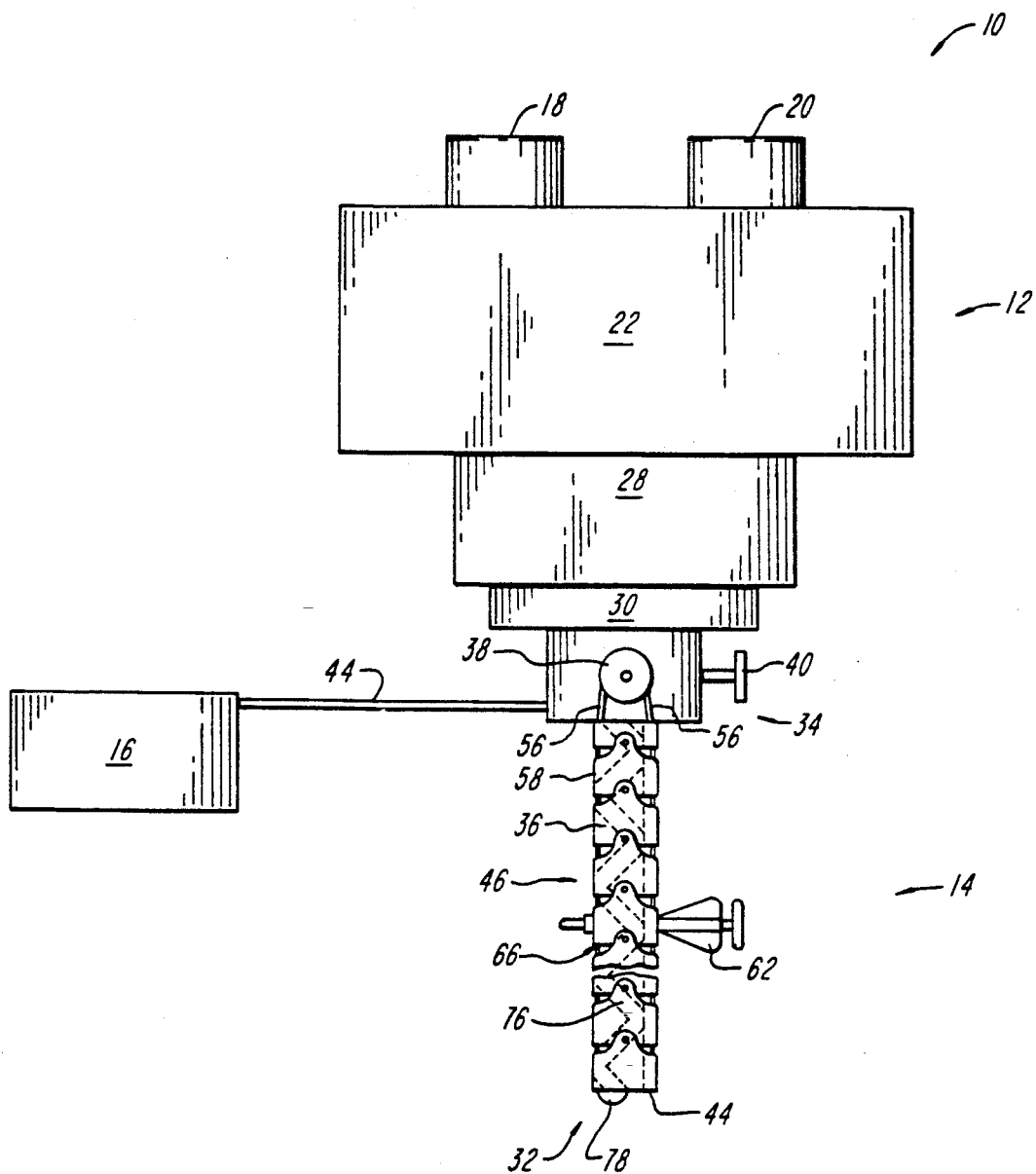
FIG. 5 is a front view of a third embodiment of the invention having a flexible sleeve containing a single lens system including a series of optically aligned prisms for transmitting an image.
Figure 6:
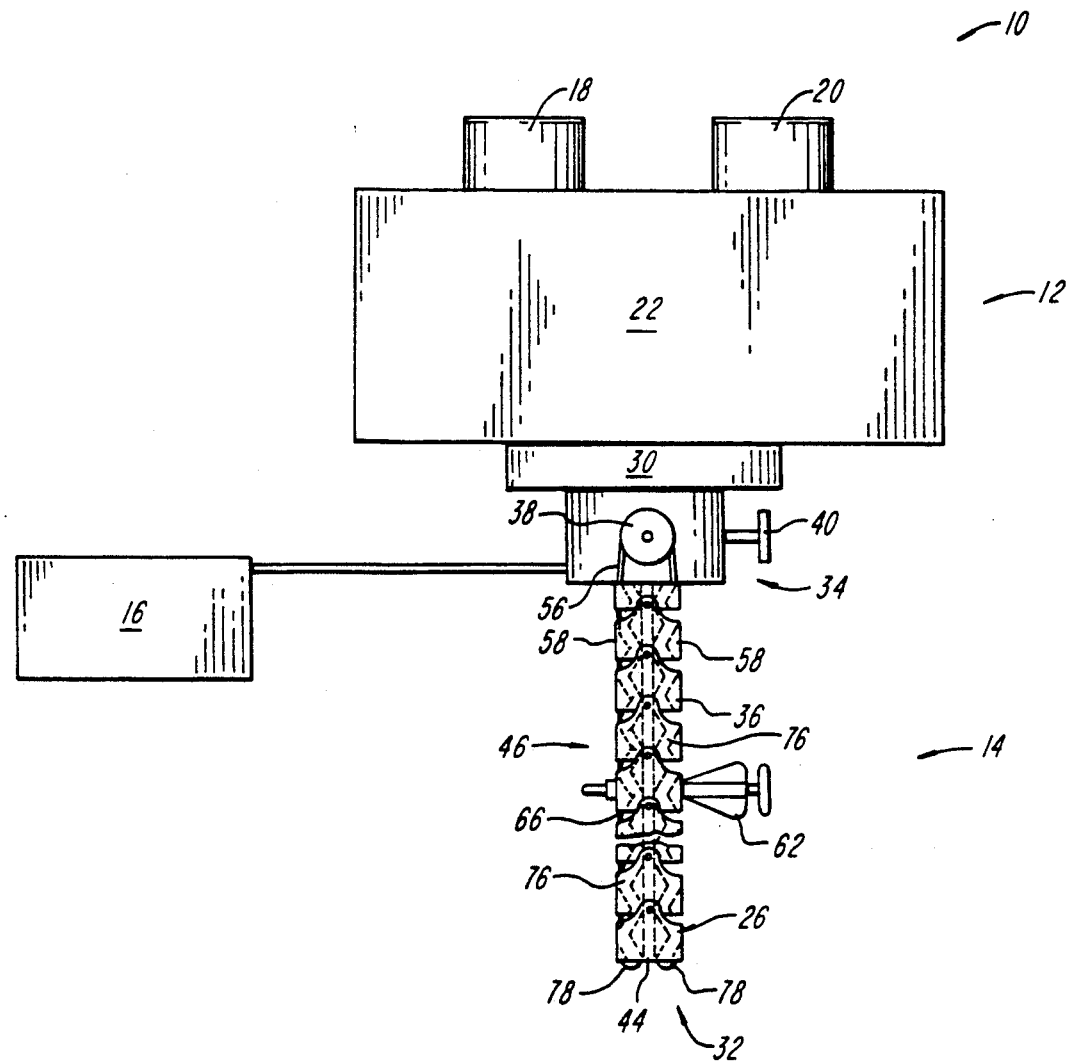
FIG. 6 is a front view of the third embodiment of the invention depicted in FIG. 5 having a pair lens systems means contained within the sleeve of the endoscope.
Figure 7:
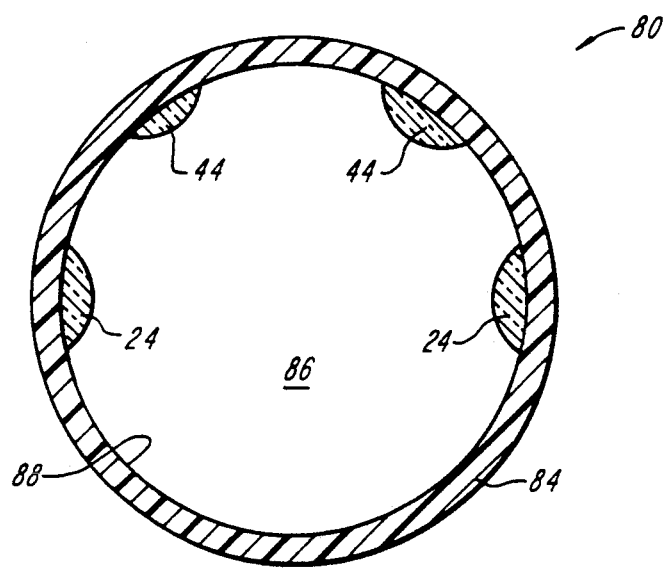
FIG. 7 is an end view of a fourth embodiment of the invention having a hollow interior with an image transmitting system mounted on the interior surface.

Referring to FIGS. 1 through 7, wherein like reference numerals refer to like parts, there is illustrated a endoscopic operating microscope 10. Microscope 10 includes a surgical microscope 12 operatively connected to an endoscope 14. The endoscope 14 can have a flexible configuration, as shown in FIGS. 1, 2, 5, and 6, or a rigid configuration, as shown in FIGS. 3, 4, and 7. A light source 16 provides illuminating light for transmission by the components of the endoscope 14.

The surgical microscope 12 preferably is configured as a free-standing unit and includes two ocular openings 18 and 20. Configuring the microscope 12 as a free-standing unit increases the freedom afforded to the user's hands through-out operation of the apparatus 10. An optical connecting means 22 optically connects the microscope 12 to the endoscope 14. More particularly, the connecting means 22 connects ocular openings 18 and 20 to the guide means 24 (FIGS. 1, 2, and 7) or lens means 66 (FIGS. 3 through 6) of the endoscope 14. When only a single guide means 24 or lens means 66 is utilized, as in the case of the embodiments of FIGS. 1, 3, and 5, the microscope 12 includes a prism means 28. The prism means 28 can be either a component of the optical connecting means 22 or, as shown in the FIGURES, a separate unit. In operation, the prism means 28 splits the image transmitted by the single guide means 24 or lens means 66 and transmits it to each of the ocular openings 18 and 20. The microscope 12 also preferably includes an image inversion system 30. Image inversion system 30 inverts the optical image transmitted by the guide means 24 or lens means 66 so that it is oriented upright for viewing.

Referring to FIGS. 1 and 2, there is shown the surgical microscope 12 connected to endoscope 14. The endoscope 14 has an insertion end 32 and observation end 34. The insertion end 32 is sized and shaped to be inserted into and retracted from an incision or body cavity. Typically the endoscope 14 has an elongate, rod-like configuration. The observation end 34 is adapted to be connected to the surgical microscope 12 and includes the controls discussed below.

Connected to the terminus of the observation end 34 are controls for maneuvering the insertion end 32 of the endoscope 14. These controls are operationally connected to the collar elements 36 discussed in detail below. Typical endoscope controls include a locking means 38 and a rotating means 40. The locking means 38 assists to secure the insertion end 32 in selected positions. The rotating means 40 allows the user to rotate the insertion end 32 about its longitudinal axis and, thus, provide the viewer with a 360 degree field of view. Connected proximate to the terminus of the observation end 34 is a light source 16. More particularly, a light source 16 is connected to an illuminating means 44 which extends into the insertion end 32. The light source 16 provides illuminating light for transmission into the cavity or incision being investigated.

The insertion end is defined by a sleeve 46 formed by a series of collar elements 36. In general, the collar elements 36 have a tubular configuration. The upper edge of each collar element 36 includes a raised portion 48 having an centrally positioned aperture 50. A pair of oppositely disposed apertures (not shown) are also cut into the lower portion of each collar element 36. Preferably, these apertures are positioned such that upon connection of sequential collar elements 36 using, for example, a pin, bolt, or other fastener 54, a flexible tube, i.e., the sleeve 46, will be formed. Accordingly, the apertures typically are positioned sufficiently close to the upper and lower edges of the collar elements 36 so as to permit adjacent units to pivot relative to each other.

The overall degree of pivoting of the elements 36, and thus flexure of the sleeve 46, is controlled by wires 56 passing through a pair of channels 58 connected to the exterior of the collar elements 36. These wires 56 are, in turn, operatively connected to the locking means 38. In operation, the locking means 38 secures the sleeve 46 in a given configuration by removing slack from the wires 56. More particularly, tightening of the locking means 38 removes slack from the wires 56. This causes the collar elements 36 to be drawn together, thus preventing further relative pivotal displacement. A safety lock 62 can be positioned on the external surface of one of the collar elements 36 of the sleeve 46 after tightening of the locking means 38. The safety lock 62 acts to prevent further accidental penetration of the sleeve 46 after it is secured in a given position.

Contained within the sleeve 46 is a guide means 24 for transmitting an image from the insertion end 32 to the observation end 34. Also contained within the sleeve 46 is an illuminating means 44. Preferably, the guide means 24 and illuminating means 44 are contained within a covering 60. The covering 60 protects the guide means 24 and illuminating means 44 from the deleterious effects of exposure to corrosive biologic fluids and potential pinching between adjacent collar elements 36. Preferably, the guide means 24 are fiber-optic bundles arranged either singularly, as shown in FIG. 1, or in pairs, as shown in FIG. 2. When used in pairs, the guide means 24 are preferably positioned on opposite sides of the illuminating means 44. Positioned on the end of each guide means 24 can be a moveable prism (not shown). The prism serves to increase the field of vision of the guide means 24. When a pair of fiber-optic bundles are utilized as the guide means 24, as in the case of the embodiment of FIG. 2, prisms having an angle of reflection of six degrees are utilized and oriented so as to form convergent fields of view. This latter configuration enhances the three-dimensional presentation of the object under investigation.

Turning to FIGS. 3 and 4, there is shown the surgical microscope 12 connected to now rigid endoscope 14. Preferably, a flexible prism means 27 connects the surgical microscope 12 to the now rigid endoscope 14. In operation, the prism means 27 serves to increase the maneuverability of the endoscope 14, thus making operation of the apparatus 10 more convenient. The structure of the microscope 12 is as discussed above. The gross configuration of the endoscope 14 remains unchanged. Since the flexible configuration discussed above has been replaced by a rigid tubular configuration, the only maneuvering control provided in this embodiment is the rotating means 40. A light source 16 continues to provide light to an illuminating means 44 which extends into the insertion end 32.

In this embodiment of the invention, the insertion end 32 is defined by a tubular rod 64 typically manufactured from aluminum. Like the sleeve 46, the rod 64 is sized to be inserted into and retracted from an incision or body cavity. Contained within rod 64 is a lens means 66 for transmitting an image from the insertion end 32 to the observation end 34. Also contained within the rod 64 is the illuminating means 44. Preferably, the lens means 66 is either a single or paired series of optically aligned lenses 68. When used in pairs, the lenses 68 are preferably positioned on opposite sides of the illuminating means 44. Positioned on the end of each lens means 66 is a moveable prism 70. The prism 70 serves to increase the field of vision of the lens means 66. A moveable mirror 72 can also be positioned on the end of the rod 64. The mirror 72 typically can be pivoted so as to further augment the field of view afforded to the user of the microscope 10. The degree to which the mirror 72 is pivoted is controlled by manipulation of a control knob 74. When a pair of optically aligned lens means 66 is utilized, as in the case of the embodiment of FIG. 4, mirror 72 is not used and the prisms 70 are designed so as to have an angle of refraction of six degrees oriented inwardly to form convergent fields of view. As noted above, this configuration enhances the three-dimensional presentation of the object under investigation.

The embodiment of the invention shown in FIGS. 5 and 6, utilizes the sleeve 46 formed by collar elements 36 to define the insertion end 32 of the endoscope 14. The structure of the microscope 12 and controls connected to the terminus of the observation end 34 are is as discussed above with regard to FIGS. 1 and 2.

A lens means 66 is contained within the sleeve 46. Also contained within the sleeve 46 is the illuminating means 44. Preferably, the lens means 66 is either a single or paired series of optically aligned prism elements 76. These prism elements 76 are shown in phantom in the FIGURES. Each prism element 76 includes two reflective surfaces oriented at ninety degrees to each other. As a result of the configuration and orientation of the reflective surfaces, the image is reflected twice within each unit before being passed onto the next prism element 76. By sequential reflection, the image is passed up the sleeve 46 until it reaches the optical elements of the microscope 12. When used in pairs, the prisms elements 76 are preferably positioned on opposite sides of the illuminating means 44. Positioned on the terminal prism element is a lens 78 having a high degree of curvature. The high degree of curvature of the lens 78 serves to increase the overall field of vision of the lens means 66. When a paired series of prism elements 76 is utilized, as in the case of the embodiment of FIG. 6, lens 78 can be ground so as to have an angle of refraction of six degrees oriented inwardly to form convergent field of view. This modification acts to enhance the three-dimensional presentation of the object under investigation.

The embodiment of the invention shown in FIG. 7 can be used as a laryngoscope. The apparatus 80 includes a hollow tube 84 which serves as the support for the guide means 24 or lens means 66 and illuminating means 44. Tube 84 is sized and shaped for insertion into, for example, a human mouth. Preferably, an interior cavity 86 of the tube 84 is of sufficient size act as a passageway for the positioning of surgical instruments. On an interior surface 88 of the tube 84 are positioned paired sets of the guide means 24 or lens means 66 discussed in detail above. A flexible connector (not shown) can be used to connect the surgical microscope 12 to the guide means 24 or lens means 66 of the apparatus 80. In operation, this flexible connector serves to increase the maneuverability of the tube 84, thus making operation of the apparatus 80 more convenient. Also positioned on the interior surface 88 are a pair of illuminating means 44. Two illuminating means 44 are required due to the larger size of the area under investigation, i.e., the throat and larynx, and the greater diameter of the interior cavity 86 of the tube 84 as compared to the sleeve 46 or rod 64. In order to permit viewing of the image provided by the guide means 24 or lens means 66, the free ends of these units are optically connected to the connecting means 22 of the microscope 12. These connections are in accord with that described above with regard to FIGS. 2 and 4.

To use the microscope 10 of the present invention, a doctor places the insertion end 32 in an incision, or passageway of the respiratory system or gastrointestinal tract. In the case of the embodiment of the invention shown in FIGS. 1, 2, 5, and 6, the doctor uses the locking means 38 to manipulate the sleeve 46 as necessary for advancement. When the embodiment of the invention depicted in FIGS. 4, 5, and 7 is utilized, however, care must be taken to proceed only along a line-of-sight path. Throughout insertion the doctor observes the advancement of the insertion end 32 by observation through the ocular openings 18 and 20. Once the insertion end 32 is positioned as desired, the sleeve 46, when used, is secured in position using the locking means 38 and safety lock 62. The configuration of the microscope 10 including the rod 64 can be secured through the use of the safety lock 62 alone. In both case the safety lock 62 acts to prevent accidental advancement of the apparatus within the biological specimen.

Having positioned the insertion end 32, or tube 84, the doctor can proceed to perform diagnostic tests and make observations regarding the specimen under investigation. For example, a laser system can be employed as the light source 16 to provide laser light for the excision of unwanted or necrotic tissue. In addition, the microscope 10 can be used to oversee and direct the actions of surgical instruments during procedures involving minute biological components.

Removal of the insertion end 32 or tube 84 is accomplished by slowly retracting the apparatus along the same path taken during insertion. Of course, in the case of the embodiment of FIGS. 1, 2, 5, and 6 the locking means 38 is first released to allow the collar elements 36 the maximum degree of pivotal freedom during removal.

It will be understood that changes may be made in the above construction and in the foregoing sequences of operation without departing from the scope of the invention. It is accordingly intended that all matter contained in the above description or shown in the accompanying drawings be interpreted as illustrative rather than in a limiting sense.

It is also to be understood that the following claims are intended to cover all of the generic and specific features of the invention as described herein, and all statements of the scope of the invention which, as a matter of language, might be said to fall therebetween.

What is claimed is:

1. A freestanding operating apparatus for presenting a stereo image of an internal area of biological specimen under observation, said operating apparatus comprising:

an endoscope sized and shaped to be insertable into and retractable from a cavity or incision in a biological specimen said endoscope having an observation end and an insertion end, said endoscope including a first lens image transmission means for non-electronically transmitting an optical image from said insertion end of said endoscope to said observation end of said endoscope and an illuminating means for transmitting light to said insertion end; and an operating stereomicroscope operatively connected to said observation end of said endoscope, said operating stereomicroscope including an optical viewing means for presenting a stereo image of said optical image optically transmitted by said first lens image transmission means.

2. The apparatus of claim 1 further including a means for locking said endoscope in a selected position after positioning in said cavity or incision.

3. The apparatus of claim 1 including a lens system means operatively connected to said operating microscope for inverting the optical image transmitted by said first lens means, said lens system being operatively connected to said observation end of said first lens means.

4. The apparatus of claim 3 wherein said lens system means further includes a prism means for splitting said image transmitted by said first lens means and wherein said optical viewing means includes a pair of viewing ports, said prism means splitting the image transmitted by said first lens means such that it is optically transmittable to each of said viewing ports.

5. The apparatus of claim 1 further including an endoscope rotating means, said rotating means providing a means for rotating said endoscope about its longitudinal axis.

6. A freestanding operating apparatus for presenting a stereo image of an internal area of a biological specimen under observation, said operating apparatus comprising:

a flexible elongate member sized and shaped to be inserted into and retracted from a cavity or incision in a biological specimen, said flexible member having an observation end and an insertion end, said flexible member including a sleeve having a guide means for transmitting an optical image and an illuminating means for transmitting light to said insertion end, said insertion end of said guide means including a moveable prism means;

a light source means operatively connected to said observation end of said illuminating means of said flexible member, said light source means supplying light for transmission by said illuminating means; and an operating stereomicroscope operatively connected to said observation end of said flexible member, said operating stereomicroscope including an optical viewing means for presenting a stereo image of said optical image.

7. The apparatus of claim 6 wherein said member is a flexible member, said sleeve being formed by a series of collar means that are pivotally connected to each other and securable in a selected position when said flexible member is operationally positioned in the biological specimen.

8. The apparatus of claim 7 further including a means for locking said sleeve means in a selected position after positioning said flexible member in said biological specimen.

9. The apparatus of claim 6 including a lens system means operatively connected to said operating microscope for inverting the optical image transmitted by said guide means, said lens system being operatively connected to said observation end of said guide means.

10. The apparatus of claim 9 wherein said guide means is a single fiber-optic bundle.

11. The apparatus of claim 10 wherein said lens system means includes a prism means for splitting said image transmitted via said fiber-optic bundle and wherein said optical viewing means includes a pair of viewing ports, said prism means splitting said image such that it is optically transmittable to each of said viewing ports.

12. The apparatus of claim 9 wherein said guide means is two fiber-optic bundles.

13. The apparatus of claim 12 including laser means for generating a laser beam, said laser beam transmittable to said insertion end via one of said illuminating means.

14. The apparatus of claim 6 including a pair of prism means and wherein said guide means is a pair of fiber-optic bundles, one of said prism means positioned at an end of each of said fiber-optic bundles, said prism means oriented to provide convergent fields of view.

15. An operating apparatus for presenting a stereo image of an internal area of a biological specimen under examination, said operating apparatus comprising:

a flexible member sized and shaped to be inserted into and retracted from a cavity or incision in a biological specimen, said flexible member having an observation end and an insertion end, said flexible member including an optical image transmitting means and an illuminating means, said optical image transmitting means being contained within a tube means, said optical image transmitting means including a series of optically aligned prism elements and a first prism means, said optically aligned prism elements transmitting an optical image from said insertion end to said observation end of said flexible member, said first prism means positioned at said insertion end of said tube means, said first prism means configured to increase the overall field of view of said prism elements, said illuminating means transmitting light from said observation end to said insertion end;

a light source means connected to said observation end of said illuminating means of said flexible member, said light source means supplying light for transmission by said illuminating means; and an operating microscope operatively connected to said observation end of said flexible member, said operating microscope including an optical viewing means for presenting a stereo image of said optical image.

16. The apparatus of claim 15 including a lens system means operatively connected to said operating microscope for inverting the optical image transmitted by said optical image transmitting means, said lens system means being operatively connected to said observation end of said optical image transmitting means.

17. The apparatus of claim 15 wherein said optical image transmitting means is a single series of said optically aligned prism elements, each said prism element including two reflective surfaces oriented at ninety degrees to each other.

18. The apparatus of claim 17 wherein said lens system means further includes a second prism means for splitting said image transmitted by said single series of said optically aligned prism elements and wherein said optical viewing means includes at least two optical viewing ports, said second prism means splitting said image such that it is optically transmittable to each of said viewing ports.

19. The apparatus of claim 15 wherein said optical image transmitting means is a series of pairs of said optically aligned prism elements, each said prism element including two reflective surfaces oriented at ninety degrees to each other.

20. The apparatus of claim 19 wherein said lens system means further includes an optical connecting means for optically connecting one of each said viewing ports to one of each of said pairs of said optically aligned prism elements.

* * * * *